United States Patent [19]

Telschow et al.

[11] Patent Number: 4,568,764

[45] Date of Patent: Feb. 4, 1986

[54] PREPARATION OF CINNAMIC ACID

[75] Inventors: Jeffrey E. Telschow, Tarrytown, N.Y.; Edmund J. Rumanowski, Dover, N.J.

[73] Assignee: Stauffer Chemical Company, Westport, Conn.

[21] Appl. No.: 691,338

[22] Filed: Jan. 14, 1985

[51] Int. Cl.$^4$ .................................. C07C 63/64
[52] U.S. Cl. ........................................ 562/495
[58] Field of Search ............................ 562/495

[56] References Cited

FOREIGN PATENT DOCUMENTS 0017467 8/1880 Fed. Rep. of Germany ...... 562/495
48-81830 11/1973 Japan ............................. 562/495

OTHER PUBLICATIONS

Othmer, Kirk Encyclopedia of Chemical Technology, 3rd Ed., vol. 6, pp. 142–149, John Wiley & Sons, N.Y., 1981.
Calloway, N. O., Chem. Rev. 17, 327, 374–378, 1935.

Primary Examiner—Paul J. Killos

[57] ABSTRACT

There is disclosed a process for the production of cinnamic acid wherein different catalysts are used. Suitable catalysts include Lewis acids, transition metal derivatives of acetic acid and halides of alkali metals.

44 Claims, No Drawings

PREPARATION OF CINNAMIC ACID

FIELD OF THE INVENTION

The present invention relates to an improved process for the production of cinnamic acid.

BACKGROUND OF THE INVENTION

Cinnamic acid, or 3-phenyl-2-propenoic acid, is an important industrial chemical. Cinnamic acid and its derivatives are used as sun screening agents, flame retardants, cosmetics, fungicides, insecticides, food preservatives, pharmaceuticals and photographic agents. Cinnamic acid has also received considerable attention recently since it is a precursor of phenylalanine, one of the ingredients in the artificial sweetener aspartame.

The most widely used commercial process for the production of cinnamic acid has used benzaldehyde, acetic anhydride and anhydrous sodium or potassium acetate in a Perkin condensation reaction. In another commercial process for the production of cinnamic acid, benzal chloride and anhydrous sodium acetate are heated to 180° to 200° C. Since benzal chloride is cheaper than benzaldehyde, this method is especially favored by manufacturers who obtain by-product benzal chloride from their benzyl chloride plants. This basic reaction, disclosed in German Pat. Nos. 17467 and 18251, required severe reaction conditions, namely 20 atmospheres pressure and temperatures above 200° C. for 10-20 hours. These severe reaction conditions are undesirable due to the attendant dangers associated with high pressure as well as for economic reasons. Furthermore, large quantities of a tarry component are produced under the above reaction conditions.

An improvement in the above described process is reported in Japanese Patent No. 48-81830 (1973) wherein the inventors in this Japanese application disclose that potassium acetate can be reacted with benzal chloride under normal pressure to produce high yields of cinnamic acid if an amine such as pyridine, quinoline or aniline is used as a catalyst. The process reported in the above Japanese patent is not easily reproducible. Present attempts to reproduce the results reported in this patent have resulted in yields of cinnamic acid significantly lower than those reported by the Japanese inventors. Moreover, under the conditions reported in the above patent, a difficultly stirrable reaction mixture is seen. In the process disclosed in the above Japanese patent, the preferred amount of potassium acetate is 4-5 moles per mole of benzal chloride. The Japanese inventors disclose that 3 moles can be used but regardless of the molar amount of potassium acetate used, the above process still requires the use of large amounts of the expensive potassium salt for the desired yields. In addition, the Japanese patent only discloses the use of aromatic amines as catalysts.

In the co-pending application of J. E. Telschow, Ser. No. 06/685353, filed Dec. 24, 1984, entitled "Preparation of Cinnamic Acid" (Attorney Docket No. C-7331/7537), there is disclosed a process for the production of cinnamic acid from a halogenated benzal derivative and a salt of acetic acid wherein the reaction is carried out in the presence of an inert diluent which increases the stirrability of the reaction.

The use of condensing agents in Friedel-Crafts synthesis is also well documented in the prior art. A complete discussion of this subject can be found in the article entitled "The Friedel-Crafts Synthesis", Chem. Rev. 17, p. 376, 1936.

None of these prior art references teach the use of new catalysts in a process for the production of cinnamic acid. Nor is there any discussion in these references teaching the use of novel catalysts to reduce the level of expensive acetate salts used in the process for the production of cinnamic acid.

SUMMARY OF THE INVENTION

In accordance with the present invention, there is disclosed a process for the production of cinnamic acid, a ring-substituted cinnamic acid and salts thereof wherein novel catalysts are used.

In one embodiment of the present invention, a Lewis acid is used as a catalyst.

In another embodiment, an acetic acid derivative of a transition metal is used as a catalyst.

In yet another embodiment, a halide of a Group I, or alkali, metal is used as a catalyst.

DETAILED DESCRIPTION OF THE INVENTION

The present invention is directed to novel catalysts which can be used in the reaction of a halogenated benzal derivative with an acetic acid derivative to produce cinnamic acid, a ring-substituted cinnamic acid and salts thereof. The above reaction can be expressed as follows:

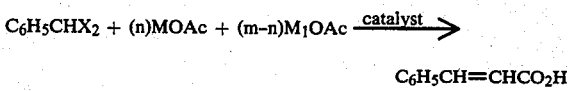

$$C_6H_5CHX_2 + (n)MOAc + (m-n)M_1OAc \xrightarrow{catalyst} C_6H_5CH=CHCO_2H$$

wherein X is halogen, i.e. Cl, Br or I, M and $M_1$ are the same or different and are alkali metals and m and n are integers from 0-3.

In the copending application of J. E. Telschow, Ser. No. 06/685353, filed Dec. 24, 1984, entitled "Preparation of Cinnamic Acid" the subject matter therein being incorporated by reference, there is disclosed an improved process wherein the reaction of a halogenated benzal derivative with an acetic acid derivative and an amine catalyst to yield cinnamic acid, a ring-substituted cinnamic acid, or salts thereof is carried out in the presence of an inert diluent which increases the stirrability of the reaction mixture.

It has now surprisingly been found that different catalysts can be used in the above-identified reaction.

The halogenated benzal derivative used in the above reaction is selected from the group consisting of benzal chloride, benzal bromide and benzal iodide. A preferred compound is benzal chloride.

The halogenated benzal derivative can in addition be ring-substituted with additional sterically compatible groups which are non-reactive under the conditions of the reaction such as chloro, fluoro, nitro, cyano, alkyl, alkoxy, alkylthio, aryl, alkyl substituted aryl, alkoxy substituted aryl or aryloxy. Thus, when the above ring-substituted halogenated benzal derivative is used in the reaction of the present invention, a ring-substituted cinnamic acid would be produced.

By the term "acetic acid derivative" is meant acetic acid as well as salts of acetic acid, sodium acetate, potassium acetate and the like. Particularly preferred acetic acid derivatives used in the present invention are alkali metal derivatives of acetic acid, i.e. sodium acetate and potassium acetate. The amount of the acetic acid derivative used can range from about 2 to about 5 moles of the acetic acid derivative per mole of halogenated benzal derivative. In a preferred embodiment of the invention, the sodium and potassium derivatives of acetic acid are used in a 2:1 ratio of the sodium derivative to the potassium derivative. Thus, the reaction is run using a 3 mole acetic acid derivative/1 mole halogenated benzal derivative ratio. Hereinafter, the term "acetic acid derivative" is defined to mean a single acetic acid derivative or combinations of salts of acetic acid.

In one embodiment of the present invention, a Lewis acid is used as a catalyst. The term "Lewis acid" is well known to those skilled in the art to which the present invention pertains. A concise definition of the term "Lewis acid" can be found at Morrison and Boyd, *Organic Chemistry*, Fourth Edition, p. 37, wherein a Lewis acid is defined as a substance which can take up an electron pair to form a convalent bond. Hereinafter, the terms "Lewis acid" or "Lewis type acid" will refer to substances meeting the above definition.

The Lewis acid can be any substance falling within the previously defined class. Additionally, the Lewis acid catalyst employed in the present invention may, though not necessarily, be a metal halide and may be essentially anhydrous.

Non-limiting examples of Lewis acids suitable for use in the present invention include stannic chloride, zinc chloride, titanium tetrachloride, ferric chloride, zirconium tetrachloride and aluminum chloride. Similarly, other halides of transition metals may be used as catalysts in the above reaction. The exact mechanism through which the Lewis acid asserts its catalytic effect is not known but it is believed that the Lewis acid may promote the dissociation of the halogen atom(s) from the halogenated benzal derivative.

The amount of catalyst employed in the present invention is dependent upon the particular catalyst chosen. Generally, increasing amounts of catalyst will increase the yield of the desired product. Generally, a molar ratio of from about 2 mole percent to about 10 mole percent based on the halogenated benzal derivative is used in the present reaction.

In another embodiment of the present invention, a transition metal acetic acid derivative is used as a catalyst. Non-limiting examples of suitable transition metal derivatives of acetic acid include zinc acetate, cupric acetate, ferric acetate, etc.

The amount of transition metal derivatives of acetic acid catalyst can range from about 4 mole percent to about 12 mole percent based on the halogenated benzal derivative. Higher or lower amounts may also be used depending upon the particular catalyst chosen.

In yet another embodiment of the present invention, the catalyst employed is a halide of a Group I element. By "Group I element" is meant those elements appearing in Group I of the Periodic Table. Non-limiting examples of suitable Group I halides include the iodide and bromide derivatives of sodium, potassium and lithium. A preferred catalyst of the above class used in the present invention is potassium iodide.

The amount of a halide of a Group I, or alkali, metal employed as catalyst in the present invention can range from about 1 to about 10 mole percent based on the halogenated benzal derivative.

Inert diluents used in the present invention include any diluent which increases the stirrability of the reaction. Non-limiting examples of inert diluents include mineral oil, tetralin and high boiling hydrocarbons. The amount of inert diluent used is not critical and amounts ranging from about 0.5 to about 5 milliliters of diluent per milliliter of reaction mixture may be used.

The temperature at which the reaction is carried out can range from about 145° to about 190° C. An especially preferred temperature at which the process of the present invention is carried out is about 180° C.

The reaction time can range from about 10 to about 35 hours. A preferred reaction time for the process of the present invention is about 17 hours.

The order in which the reactants are added is not critical. The halogenated benzal derivative, acetic acid derivative and catalyst can be added to the inert diluent or the inert diluent can be added to a mixture of the halogenated benzal derivative, catalyst and acetic acid derivative.

The process of the present invention is carried out in an inert atmosphere such as nitrogen.

The stirring of the reaction mixture can be accomplished by using a mechanical stirrer.

At the conclusion of the reaction, usually after about 15–20 hours, the cinnamic acid, ring-substituted cinnamic acid, and/or salt form thereof, remains in the thick mixture. The mixture is then diluted with water and basified using a known amount of caustic. The basified solution is separated and then acidified with a known amount of hydrochloric acid. Conventional extraction, filtering and washing techniques well known to those skilled in the art are then used to purify the desired product.

The present invention is illustrated by the following non-limiting examples.

EXAMPLE 1

This Example illustrates the use of stannic chloride as a catalyst.

To a 500 milliliter, 3 necked flask were added 115 milliliters of Kaydol ® mineral oil and 40.3 grams (0.25 mole) of benzal chloride. The mixture was heated to 80° C. and then 41 grams (0.6 mole) of sodium acetate, 24.5 grams (0.3 mole) of potassium acetate and 2.6 grams of stannic chloride (4 mole percent based on benzal chloride) were added.

The mixture was heated in an oil bath at from about 177° to about 182° C. for 17 hours. At the end of the 17 hour heating period, the reaction mixture was allowed to cool to 120° C. and 200 milliliters of hot water was added.

The pH of the reaction mixture was adjusted to 10 with 25 milliliters of 50 percent caustic. The mixture was then poured into a separatory funnel wherein solids separated out. One hundred milliliters of hot water (50° C.) was then added. The mixture was heated to 90° C. and 25 milliliters more of hot water was added. The lower water layer was separated off from the Kaydol mineral oil upper layer. The water layer was then cooled to 60° C. and 80 milliliters of 32 percent HCl was added to bring the pH to 2. The mixture was then cooled to room temperature and the cinnamic acid was filtered off.

To the upper mineral oil layer was added 500 milliliters of hot water and the mixture was heated to 60° C. The mixture was poured into a separatory funnel, the lower water layer separated, reacidified to pH 2, cooled and filtered. A 59 percent yield of cinnamic acid was obtained from the two crops.

EXAMPLE 2

Similar to Example 1 except 1.3 grams (2 mole percent based on benzal chloride) of stannic chloride was used as a catalyst. After basification, extraction and acidification as detailed in Example 1, a 51 percent yield of cinnamic acid was obtained.

EXAMPLE 3

Similar to Example 1 except 3.8 grams (8 mole percent based on benzal chloride) of titanium tetrachloride was used as a catalyst. After basification, extraction and acidification, a 47 percent yield of cinnamic acid was obtained.

EXAMPLES 4

Similar to Example 3 except 1.9 grams (4 mole percent based on benzal chloride) of titanium tetrachloride was used as a catalyst. After following the procedures set forth previously, a 44 percent yield of cinnamic acid was obtained.

EXAMPLE 5

Similar to Example 1 except 3.2 grams (8 mole percent based on benzal chloride) of ferric chloride was used as a catalyst. After extraction and purification procedures, a 42 percent yield of cinnamic acid was obtained.

EXAMPLE 6

Similar to Example 5 except 1.6 grams (4 mole percent based on benzal chloride) of ferric chloride was used as a catalyst. After extraction and purification procedures, a 53 percent yield of cinnamic acid was obtained.

EXAMPLE 7

Similar to Example 6 except 0.8 grams (2 mole percent based on benzal chloride) of ferric chloride was used as a catalyst. After extraction and purification procedures, a 25 percent yield of cinnamic acid was obtained.

EXAMPLE 8

Similar to Example 1 except 2.3 grams (4 mole percent based on benzal chloride) of zirconium tetrachloride was used as a catalyst. After extraction and purification procedures, a 40 percent yield of cinnamic acid was obtained.

EXAMPLE 9

Similar to Example 1 except 2.6 grams (8 mole percent based on benzal chloride) of zinc chloride was used as a catalyst. After extraction and purification procedures, a 32 percent yield of cinnamic acid was obtained.

EXAMPLE 10

Similar to Example 1 except 1.3 grams (4 mole percent based on benzal chloride) of aluminum chloride was used as a catalyst. After extraction and purification procedures, a 6 percent yield of cinnamic acid was obtained.

EXAMPLE 11

This example illustrates the use of an acetate salt of a transition metal as a catalyst. Similar to Example 1 except 3.0 grams (6.7 mole percent based on benzal chloride) of zinc acetate was used as a catalyst. After extraction and purification procedures, a 38 percent yield of cinnamic acid was obtained.

EXAMPLE 12

Similar to Example 11 except 2.0 grams (4 mole percent based on benzal chloride) of cupric acetate was used as a catalyst. After extraction and purification procedures, a 39 percent yield of cinnamic acid was obtained.

EXAMPLE 12

This example illustrates the use of a halogenated alkali metal as a catalyst. Similar to Example 1 except 3.2 grams (10 mole percent based on benzal chloride) of potassium iodide was used as a catalyst. After extraction and purification procedures, a 39 percent yield of cinnamic acid was obtained.

Additional features of the preferred and most preferred embodiments of the present invention are found in the claims hereinafter.

What is claimed is:

1. A process for the production of cinnamic acid, a ring-substituted cinnamic acid, and salts thereof from a halogenated benzal derivative and acetic acid derivative in an inert diluent which comprises the use of a Lewis type acid as a catalyst.

2. A process according to claim 1 wherein the temperature is from about 145° C. to about 190° C.

3. A process according to claim 1 wherein the halogenated benzal derivative is benzal chloride, benzal bromide or benzal iodide.

4. A process according to claim 3 wherein the halogenated benzal derivative is benzal chloride.

5. A process according to claim 1 wherein the inert diluent is selected from the group of high boiling hydrocarbons consisting of tetralin, decalin and mineral oil.

6. A process according to claim 5 wherein the inert diluent is tetralin.

7. A process according to claim 5 wherein the inert diluent is decalin.

8. A process according to claim 5 wherein the inert diluent is mineral oil.

9. A process according to claim 1 wherein said halogenated benzal derivative comprises a 1:3 ratio of halogenated benzal derivative to acetic acid derivative.

10. A process according to claim 9 wherein the halogenated benzal derivative is benzal chloride, benzal bromide and benzal iodide.

11. A process according to claim 10 wherein the halogenated benzal derivative is benzal chloride.

12. A process according to claim 1 wherein said acetic acid derivative is an alkali metal derivative of acetic acid.

13. A process according to claim 12 wherein said alkali metal derivative of acetic acid comprises a 2:1 ratio of sodium acetate to potassiuum acetate.

14. A process according to claim 1 wherein said Lewis acid catalyst is a halide of a transition metal.

15. A process according to claim 14 wherein said Lewis acid is stannic chloride.

16. A process according to claim 14 wherein said Lewis acid is titanium tetrachloride.

17. A process according to claim 14 wherein said Lewis acid is ferric chloride.

18. A process according to claim 14 wherein said Lewis acid is zirconium tetrachloride.

19. A process according to claim 14 wherein said Lewis acid is aluminum chloride.

20. A process for the production of cinnamic acid, a ring-substituted cinnamic acid, and salts thereof from a halogenated benzal derivative and an acetic acid derivative in an inert diluent which comprises using a transition metal derivative of acetic acid as a catalyst.

21. A process according to claim 20 wherein the temperature is from about 145° to about 190° C.

22. A process according to claim 20 wherein said inert diluent is tetralin, decalin and mineral oil.

23. A process according to claim 22 wherein the inert diluent is tetralin.

24. A process according to claim 22 wherein the inert diluent is decalin.

25. A process according to claim 22 wherein the inert diluent is mineral oil.

26. A process according to claim 20 wherein said halogenated benzal derivative comprising a 1:3 ratio of halogenated benzal derivative to acetic acid derivative.

27. A process according to claim 26 wherein said halogenated benzal derivative is selected from the group consisting of benzal chloride, benzal bromide and benzal iodide.

28. A process according to claim 27 wherein said halogenated benzal derivative is benzal chloride.

29. A process according to claim 20 wherein said acetic acid derivative is an alkali metal derivative of acetic acid.

30. A process according to claim 29 wherein said alkali metal derivative of acetic acid comprises a 2:1 ratio of sodium acetate to potassium acetate.

31. A process according to claim 25 wherein said acetic acid derivative of a transition metal catalyst is zinc acetate.

32. A process according to claim 20 wherein said acetic acid derivative of a transition metal catalyst is cupric acetate.

33. A process for the production of cinnamic acid, a ring-substituted cinnamic acid and/or salts thereof from a halogenated benzal derivative and an acetic acid derivative in an inert diluent which comprises using a halide of an alkali metal as a catalyst.

34. A process according to claim 33 wherein the temperature is from about 145° to about 190° C.

35. A process according to claim 32 wherein the inert diluent is tetralin, decalin or mineral oil.

36. A process according to claim 35 wherein the inert diluent is tetralin.

37. A process according to claim 35 wherein the inert diluent is decalin.

38. A process according to claim 35 wherein the inert diluent is mineral oil.

39. A process according to claim 33 wherein said halogenated benzal derivative comprises a 1:3 ratio of halogenated benzal derivative to acetic acid derivative.

40. A process according to claim 39 wherein the halogenated benzal derivative is selected from the group consisting of benzal chloride, benzal iodide and benzal bromide.

41. A process according to claim 40 wherein the halogenated benzal derivative is benzal chloride.

42. A process according to claim 33 wherein said acetic acid derivative is an alkali metal derivative of acetic acid.

43. A process according to claim 42 wherein said alkali metal derivative of acetic acid comprises a 2:1 ratio of sodium acetate to potassium acetate.

44. A process according to claim 33 wherein said halide of an alkali metal catalyst is potassium iodide.

* * * * *

UNITED STATES PATENT AND TRADEMARK OFFICE
CERTIFICATE OF CORRECTION

PATENT NO. : 4,568,764
DATED : February 4, 1986
INVENTOR(S) : J. E. Telschow et al.

It is certified that error appears in the above—identified patent and that said Letters Patent is hereby corrected as shown below:

<u>Col. 1, line 9</u>, "3-phenyl-2-propenoic" should read
-- 3-phenyl-2-propanoic --;

<u>Col. 5, line 15</u>, "EXAMPLES 4" should be -- EXAMPLE 4 --; and

<u>Col. 7, line 19</u>, "comprising" should be -- comprises --.

Signed and Sealed this

Twenty-seventh Day of May 1986

[SEAL]

Attest:

DONALD J. QUIGG

Attesting Officer

Commissioner of Patents and Trademarks